United States Patent [19]

Huang et al.

[11] Patent Number: 5,283,122
[45] Date of Patent: * Feb. 1, 1994

[54] FUSED LIPOSOME AND ACID INDUCED METHOD FOR LIPOSOME FUSION

[75] Inventors: Leaf Huang; Jerome Connor, both of Knoxville, Tenn.

[73] Assignee: University of Tennessee Research Corporation, Knoxville, Tenn.

[*] Notice: The portion of the term of this patent subsequent to Dec. 6, 2005 has been disclaimed.

[21] Appl. No.: 836,125

[22] Filed: Feb. 14, 1992

Related U.S. Application Data

[63] Continuation of Ser. No. 181,268, Apr. 13, 1988, abandoned, which is a continuation of Ser. No. 602,177, Apr. 19, 1984, Pat. No. 4,798,663.

[51] Int. Cl.$^5$ .............................................. A61K 9/127
[52] U.S. Cl. ................................. 428/402.2; 264/4.1; 264/4.3; 264/4.6; 424/450; 435/172.3; 436/829; 935/54
[58] Field of Search .......................... 264/4.1, 4.3, 4.6; 428/402.2; 424/450; 436/829

[56] References Cited

U.S. PATENT DOCUMENTS

| | | | |
|---|---|---|---|
| 4,235,871 | 11/1980 | Papahadjopoulos et al. | 424/450 X |
| 4,515,736 | 5/1985 | Deamer | 264/4.3 |
| 4,534,899 | 8/1985 | Sears | 260/403 |
| 4,619,794 | 10/1986 | Hauser | 264/4.1 |
| 4,789,633 | 12/1988 | Huang et al. | 435/240.1 |

*Primary Examiner*—Richard D. Lovering
*Attorney, Agent, or Firm*—George W. Neuner; Ernest V. Linek

[57] ABSTRACT

Liposomes containing phosphatidylethanolamine, palmitoyl homocysteine or oleic acid or palmitic acid, fuse rapidly when the pH of the medium is reduced below 7. Liposome fusion was measured by (a) mixing of the liposomal lipids as shown by resonance energy transfer, (b) gel filtration and (c) electron microscopy. The presence of phosphatidylethanolamine or acid addition esters thereof in the liposomes greatly enhances fusion; whereas the presence of phosphatidylcholine inhibits fusion. During fusion of liposomes containing phosphatidylethanolamine:palmitoyl homocysteine (8:2), almost all of the encapsulated calcein is released. Inclusion of cholesterol (40%) in the liposomes substantially decreases leakage without impairing fusion. Those pH sensitive liposomes are fused to deliver biologically active molecules such as DNA, into living cells.

20 Claims, 3 Drawing Sheets

FUSED LIPOSOME AND ACID INDUCED METHOD FOR LIPOSOME FUSION

CROSS REFERENCE TO RELATED APPLICATIONS

The present application is a continuation of U.S. Ser. No. 07/181,268, filed Apr. 13, 1988, now abandoned, which in turn is a continuation of U.S. Ser. No. 06/602,177, filed Apr. 19, 1984, now U.S. Pat. No. 4,798,663.

FIELD OF THE INVENTION

This invention is directed to fused liposomes, the pH controlled fusion of liposomes, and to the use of these liposomes as carriers for pharmaceutical or like agents. Liposomes composed of, for example, phosphatidylethanolamine and palmitoyl homocysteine fuse rapidly when the pH of the liposome medium is made acidic.

BACKGROUND OF THE INVENTION

Liposomes are vesicles composed of one or more lipid bilayers completely surrounding an internal aqueous space. They are usually made up of phospholipids or other amphipathic molecules either in pure form or in combination with other molecules such as sterols, long chain acids or bases, or membrane proteins. Liposomal structures vary from large (0.5 to 5 micron) multilamellar vesicles to small (250-750 angstrom) unilamellar vesicles. By convention, liposomes are categorized by size and a three letter acronym is used to designate the type of liposome being discussed. Multilamellar vesicles are generally designated (MLV). Small unilamellar vesicles are designated (SUV) and large unilamellar vesicles are designated (LUV). In each case, the chemical composition is generally given following the acronym. See: D. Papahadjopoulos, *Ann. N.Y. Acad. Sci.*, 308 1 (1978) and *Ann. Rpts. Med. Chem.*, 14 250 (1979) the disclosures of which are incorporated herein by reference.

Liposomal preparations have been made by a number of techniques, including: ethanol injection, (Batzri et al., *Biochim. Biophys. Acta*, 298 1015 (1973)); ether infusion, (Deamer et al., *Biochim. Biophys. Acta*, 443 629 (1976) and Schieren et al., *Biochim. Biophys. Acta*, 542 137 (1978)), detergent removal, (Razin, *Biochim. Biophys. Acta*, 265 241 (1972)), solvent evaporation, (Matsumato et al., *J. Colloid Interface Sci.*, 62 149 (1977)), evaporation of water in oil (REV) emulsions, (Szoka Jr. et al., *Proc. Natl. Acad. Sci. USA*, 75 4194 (1978)) and extrusions of MLV or LUV through a nucleopore polycarbonate membrane (Olson et al., *Biochim. Biophys. Acta*, 557 9 (1979)).

Liposomes may be used to affect cell behavior in vitro and in vivo. Magee and Miller (*Nature*, 235 339 (1972)) first reported that liposomes carrying antiviral antibody could protect cells against viral infection. Similar observations regarding liposomal protection of cells were noted by Gregoriadis and Buckland (*Nature*, 244 170 (1973)) who found that liposomes containing invertase could cause the disappearance of vacuoles of stored sucrose in mouse peritoneal macrophages. Papahadjopoulos and coworkers (*Biochim. Biophys. Acta*, 323 23 (1973)) reported that liposomes could induce cell fusion without cytotoxic effects.

Liposomes have been used to effect the cellular uptake of impermeant molecules, i.e., molecules that are not normally taken up. This action makes liposomes useful as carriers of foreign matter, such as drugs. For example, cyclic AMP inhibition of 3T3 cells growth in vitro was enhanced by 1000 fold using liposomes as the carrier (Papahadjopoulos et al., *Nature*, 252 163 (1974) and Papahadjopoulos et al., *Biochim. Biophys. Acta*, 363 404 (1974)). A similar increase in effectiveness was reported with actinomycin D in liposomes against a hamster cell line otherwise resistant to the drug (Papahadjopoulos et al., *Cancer Res.*, 36 4406 (1976)).

Membrane fusion under moderately acidic conditions is responsible for the infection of a number of the enveloped viruses, including Semliki Forest virus (Marsh, et al., *Cold Spring Harbor Symp. Quant. Biol.*, 46 835 (1982) and White et al., *J. Cell Biol.* 89 674 (1981)), vesicular stomatitis virus and influenza virus (White et al., supra). The precise mechanism of the acid induced membrane fusion is not known. Studies with liposome membranes have revealed that liposomes made of azolectin can fuse with the mitochondria inner membranes at PH 6.5 (Schneider et al., *Natl. Acad. Sci. USA*, 77 442–446 (1980)). Serum albumin (Schenkman et al., *Chem. Phys. Lipids*, 649 633 (1981) and Schenkman et al., *Chem. Phys. Lipids*, 28 165 (1981)) and its proteolytic fragments (Chaimovich et al., *Biophys. J.*, 41 28a (1983)) can induce liposome fusion at a pH below 4. Blumenthal et al. have shown that clathrin induces the fusion of neutral liposomes at a pH below 6.5 (Blumenthal et al., *Biol. Chem.* 258 3409 (1983)). In all these cases, liposome fusion requires the presence of some protein or other macromolecule.

Allens et al., (*J. Cell Biol.*, 97 10)(a), Abstr. No. 419 (1983)) reported liposomes containing phosphatidylethanolamine and cholesterylhemisuccinate which are sensitive to pH in the endosomal PH region. These liposomes fuse with the endosomal membrane upon acidification of the endosome and thus deliver their contents to the cytoplasm.

Straubinger and coworkers (*J. Cell Biol.*, 97 109(a), Abstr. No. 420 (1983)) reported the preparation of liposomes which became unstable at mildly acidic PH. These liposomes, which were composed of oleic acid, phosphatidylethanolamine and cholesterol (3:7:3 mol ratio), became permeable to the anionic fluorescent dye, calcein, below pE 7.0. These liposomes promoted the delivery of entrapped calcein to the cytoplasm of CV-1 cells.

SUMMARY OF THE INVENTION

This invention is directed to (1) fused liposomes, (2) a process for the fusion of liposomes and (3) the use of these liposomes for cellular microinjection, i.e. delivery, of pharmaceutical or other agents. Liposomes, made to be PH sensitive, are fused when their medium is treated to make the pH acidic. These liposomes become pH sensitive when greater than about 20 mol percent of an amphipathic molecule containing one or more weakly acidic functional groups, such as the carbokylic group. Compounds of this type include palmitoylhomocysteine and long chain, i.e., $C_{12}$ to $C_{30}$, preferably $C_{16}$ to $C_{24}$, fatty acids such as palmitic acid and oleic acid. The presence of an amphipathic molecule which has a tendency to form hexagonal phase or inverted micelles, such as phosphatidylethanolamine, greatly enhances this fusion process. In one demonstrated example, infra, a preferred mole ratio of phosphatidylethanolamine to palmitoyl homocysteine is 8:2.

DETAILED DESCRIPTION

Figure 1:
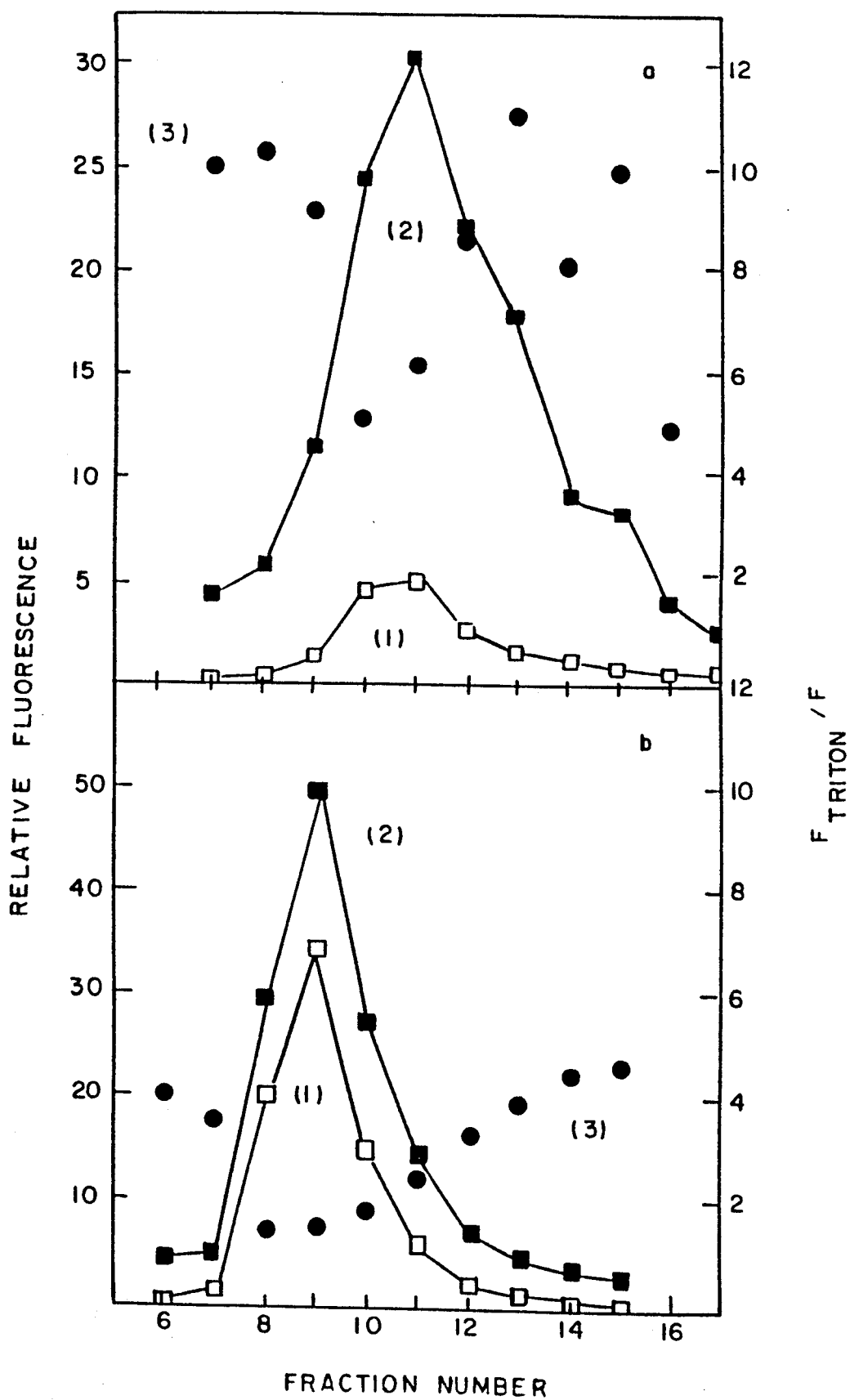
FIG. 1 depicts a graph of the Biogel A.50M gel filtration of liposomes before (a) and after (b) the acid treatment. Labelled and unlabelled liposomes were mixed at a lipid concentration of 200 microM and n=3. Fractions were measured for fluorescence of N-NBD-PE (lambda$_{ex}$=468 nm, lambda$_{em}$=530 nm) in the absence (1) and presence (2) of 0.2% Triton X-100. The ratio (3) of fluorescence in the presence and absence of Triton is also plotted.

The following abbreviations are used herein:
PHC—palmitoyl homocysteine
PE—phosphatidylethanolamine
N-NBD-PE—N-(7-nitro-2,-1,3-benzoxadiazol-4-yl)-PE
N-Rh-PE—N-(lisamine rhodamine B-sulfonyl)-PE
PC—phosphatidylcholine
PA—palmitic acid
PS—phosphatidylserine
OA—oleic acid
chol—cholesterol
PBS—phosphate buffered saline.

The present invention is the first demonstration of an acid induced liposome fusion which is not mediated by proteins or other macromolecules. In the case of liposome fusion mediated by proteins, e.g. serum albumin (Schenkman et al., *Biochim. Biophys. Acta*, supra and Chaimovich, supra), clathrin (Blumenthal, supra) and viral glycoproteins (White, supra; White et al., *Proc. Natl. Acad. Sci. USA*, 77 3272 (1980); and Marsh et al., *J. Cell Biol.*, 96 455 (1983)), it is clear that the protein conformational change is the primary driving force for fusion. In the method of the present invention the driving force comes from the lipid itself. Homocysteine forms a thiolactone ring at acidic pH (Baernstein *J. Biol. Chem.*, 106 451 (1934)). This mechanism was thought to be responsible for the pH-sensitive leakage in liposomes composed of disaturated PC and PHC (Yatvin et al., *Science*, 210 1253 (1980)). However, recent evidence argues against this mechanism; rather the pH effect may be explained by a change in "acid/base" equilibrium, i.e., the ratio of charged to uncharged N-acylamino acid with subsequent changes in the electrostatic interactions among the lipid headgroups. Alternatively, the bilayer solubility of the protonated PHC might be so low that domains of PHC are formed at acidic pH. Such lateral phase separation of the bilayer lipids could be a major cause of fusion (Cestaro et al., *J. Biochem.*, 133 229 (1983); Yatvin et al., in *Liposome Technology*, Gregoriadis, G. (ed.) (CRC Press, Boca Raton 1984); and Sundler et al., *Biochim. Biophys. Acta*, 649 751 (1981)). The latter mechanism appears particularly attractive because we have found that the presence of PE greatly enhances acid induced liposome fusion. Any amphipathic molecule which has a tendency to form hexagonal phase or inverted micelles such as pure unsaturated PE, and especially the dioleoyl PE used in the method of this invention, is suitable. PE is prone to form hexagonal phase or inverted micelles (Cullis et al., *Nature* (Lond.), 271 672 (1978), Cullis et al., *Biochim. Biophys. Acta*, 559 399 (1979), (Cullis et al., *Nature* (Lond.) and Lucy *Nature* (Lond.), 277 815 (1970)). Furthermore, other long chain amphiphiles containing a carboxylic group, such as fatty acids, (see FIG. 3) can also be used for acid induced liposome fusion.

The interactions of liposomes with animal cells have been extensively studied. Although liposome-cell fusion was initially suggested as a primary mechanism, recent studies in this (Huang et al., *J. Biol. Chem.*, 258 14034 (1983)) and other laboratories (Heath et al., *Proc. Natl. Acad. Sci. USA*, 80 1377 (1983); Leserman et al., *Nature* (Lond.), 293 226 (1981); and Machy et al., *J. Immunol.*, 129 2098 (1982)) show that the endocytosis of liposomes is primarily responsible for liposome uptake. Furthermore, Straubinger et al. (*Cell*, 32 1069 (1983)) have shown that endocytosed liposomes encounter an acidic environment once they enter the endosomes. The pH of endosomes has been determined to be about 5 (Tycko et al., *Cell*, 28 643 (1980)). Thus, liposomes sensitive to a pH in this endosomal region (about 5) will fuse to the endosome membrane and release their contents to the cell cytoplasm.

Sonicated liposomes containing PE and PHC fused readily when the medium PH was lowered below 7. Reducing the pH of the liposome medium may be accomplished using any technique available to the skilled artisan. The most common method available is by the addition of an acid. Generally, as used herein, the liposomal medium is a phosphate buffered saline solution, pH 7.6. To reduce this pH, a mineral acid, such as hydrochloric acid, is added. The concentration of the acid may be varied depending on the final pH desired and the volume of medium being treated. For example, as discussed infra, 5 microliters of 1N HCl when added to 2 ml of liposome suspension in phosphate buffered saline at PH 7.6, reduces the pH to 4.8, whereupon, the liposomes fuse. This fusion was measured by an increase in liposome size using negative stain electron microscopy. The diameter of the original, untreated sonicated liposomes was $4.9 \pm 2.3 \times 10^2$ angstroms. After the acid treatment (to PH 4.8), about one-third of the liposomes appeared relatively unchanged in size, i.e. in the range of 300-700 angstroms in diameter. The rest of the liposomes became much larger with a diameter of $2.9 \pm 1.1 \times 10^3$ angstroms. The fused liposomes were not aggregated. Since the increase in liposome diameter was approximately 6 fold, several rounds of fusion must have occurred.

The increase in liposome size was also measured by gel filtration (see FIG. 1). In this measurement, labelled liposomes (containing 1 mol % each of N-NBD-PE and N-Rh-PE) and 3-fold excess of unlabelled liposomes were mixed. An aliquot was chromatographed on a Biogel A50M column at pH 7.4. A heterogeneous liposome population caused the broad peak in the elution profile. Another aliquot was treated with acid (to pH 4.8) and then chromatographed on the same column after the pH was returned (using NAOH) to 7.4. The eluted liposomes were detected by the emission of N-NBD-PE as measured at 530 rim. The fluorescence of each fraction was also measured in the presence of 0.2% Triton X-100 to completely dissolve the liposomes. As can be seen, the sonicated liposomes, originally eluted in the included volume fractions of the column, had shifted to the void volume fractions (fraction 9) after the acid treatment, indicating an increase in liposome size. Furthermore, the ratio of N-NBD-PE fluorescence in the presence and absence of Triton X-100 was very different in these liposomes. Before fusion, the ratios were generally greater than 5, indicating a high degree of quenching of the N-NBD-PE fluorescence due to efficient energy transfer. After the acid treatment, these ratios were significantly reduced to below 5, indicating less efficient energy transfer. This result was expected if the acid treatment induced a fusion between the labelled and the unlabelled liposomes. This would result in a dilution of the fluorescent probes in the fused membranes.

Figure 2:
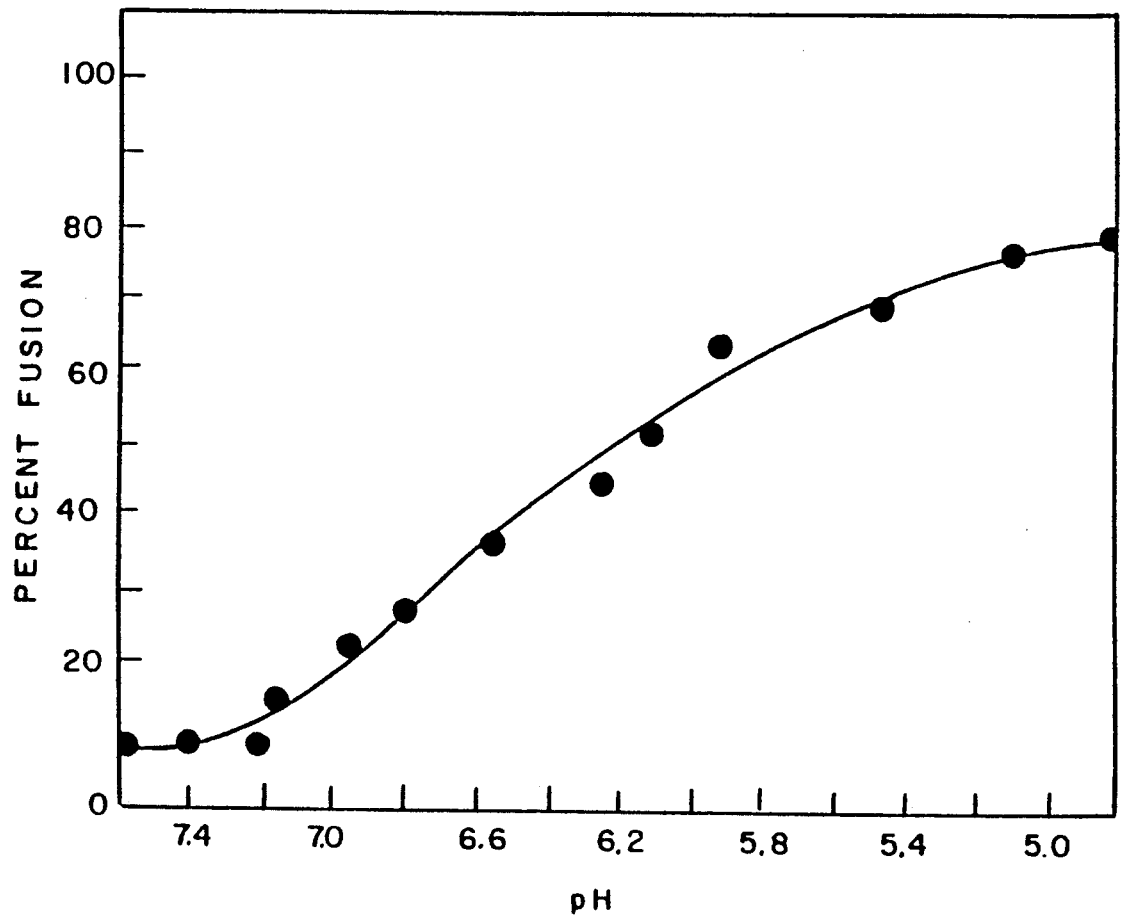
FIG. 2 depicts a graph of the pH dependence (from pH 4.8 to 7.6, particularly pH 4.8 to 6.8) of liposome fusion. PE:PHC (8:2) liposomes were fused at a lipid concentration of 200 microM and n=3. Percent fusion was calculated according to eq. (1)

The acid induced liposome fusion could be quantitated by the resonance energy transfer method originally described by Struck et al., (*Biochem.*, 20 4093 (1981)). In this assay, the extent of fusion was measured by the dilution of the fluorescent probes embedded in the membranes. As shown in FIG. 2, the percent fusion, as calculated by using eq. (1), for PE:PHC (8:2) liposomes was dependent on the pH of the medium. Fusion occurred when pH was below 7.0 and reached maximum at pH=4.8–5.0 with a mid-point pH=6.2.

The lipid composition of the liposome strongly determined the efficiency of the acid induced fusion. Table I shows the percent fusion at pH 4.8 for liposomes made of various lipid compositions. From the data shown, it was determined that the presence of PHC was required for fusion. The combination of PE and PHC (8:2) was very effective for fusion; whereas the addition of PC to such liposomes diminished fusion. Fusion was reduced from 89 to 36% when 25% of the PE (PE:PC:PHC=6:2:2) was replaced by PC. The maximal fusion was observed with liposomes containing large amounts of PE and no PC. Fusion percentages of less than 20% were deemed not significant.

Figure 3:
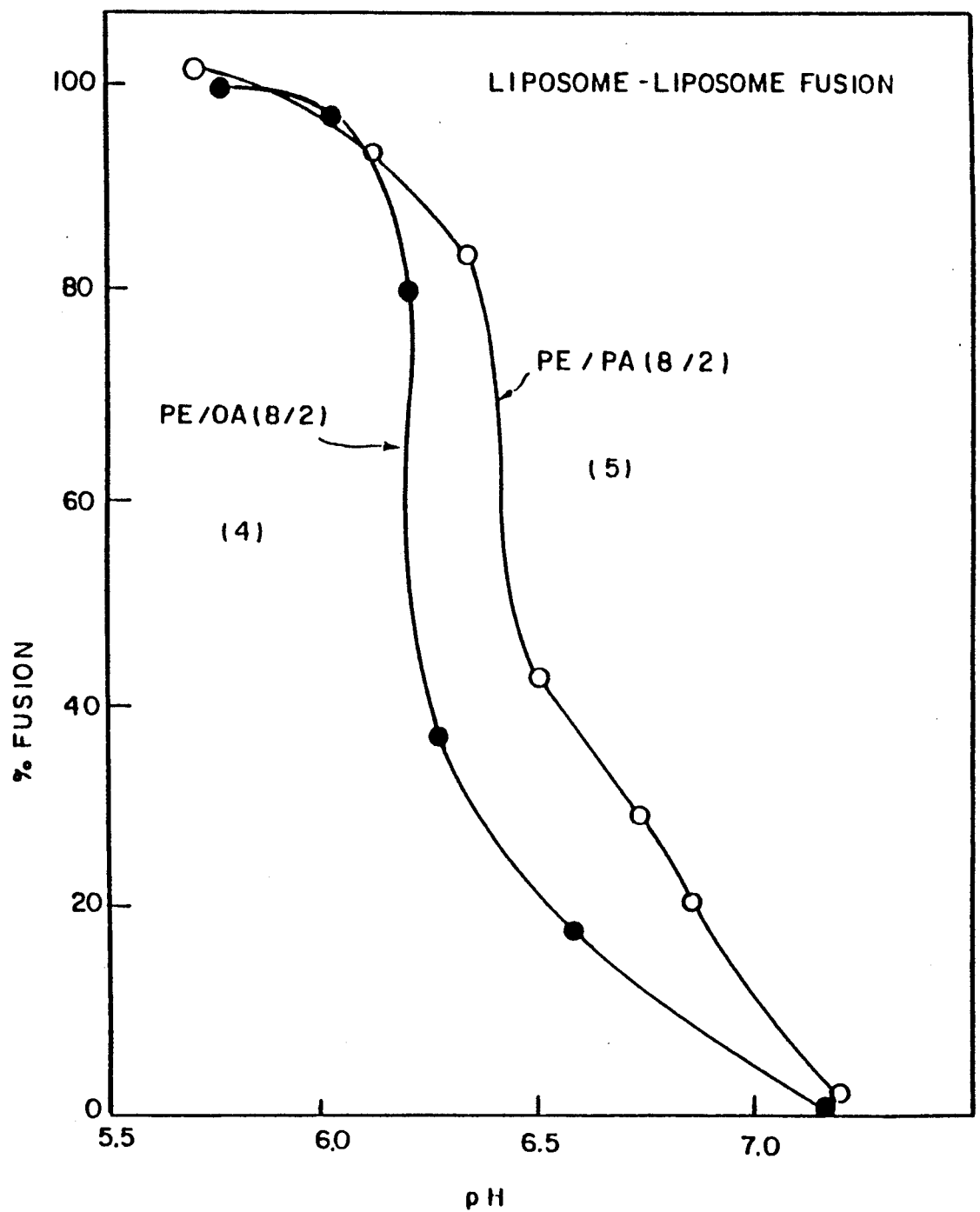
FIG. 3 depicts liposome fusion percentage as a function of pH (from pH 5.5 to 7.5, particularly pH 5.75 to 6.0) for phoshatidylethanolamine-oleic acid (8:2) treated liposomes (4) and phosphatidylethanolamine-palmitic acid (8:2) treated liposomes (5).

In addition to the PE-PHC composition liposomes, other lipids were evaluated for their effect on pH sensitivity toward liposome fusion. For example, as shown in FIG. 3, liposomes containing phosphatidylethanolamine (PE) and palmitic acid (PA) in a molar ratio of 8:2 demonstrated a dramatic rate and percentage of fusion at about pH 6.3 and below. This is to be contrasted with the steady, almost straight line increase in fusion for liposomes containing PE-PHC (8:2) as a function of pH, shown in FIG. 2.

In addition to liposomes containing PE/PA (8:2), liposomes contining PE and oleic acid (OA) (8:2) were studied (see FIG. 3). These liposomes, like those containing PE/PA demonstrated a rapid fusion rate and percentage at about pH 6.3 and below.

Each of these pH sensitive liposome types (gradual fusion or rapid fusion) has its advantages and disadvantages as a transport agent for cellular microinjection. For example, the gradual fusion liposomes, such as the PE:PHC (8:2) liposomes will transport their contents over a wide range of pH existing in the various endosomes of cells. However, due to the fusion limits at higher pH levels, infusion at higher pH will be low. On the other hand, the liposomes such as those containing PE/PA (8:2) and PE/OA (8:2), which fuse only at a certain pH, will be totally ineffective at a pH above their threshold point—a pH level some cells may not have at all.

TABLE I

| Acid Induced Fusion of Liposomes of Various Compositions* | | |
|---|---|---|
| Lipid composition | | Fusion+ % |
| PE:PHC | (8:2) | 89.0 ± 2.14 |
| PE:PHC | (6:4) | 53.0 ± 1.58 |
| PE:PHC | (3:7) | 62.0 ± 1.87 |
| PE:PC:PHC | (6:2:2) | 36.0 ± 1.29 |
| PE:PC:PHC | (4:4:2) | 21.0 ± 2.01 |
| PC:PHC | (8:2) | 8.0 ± 1.00 |
| PS:PHC | (8:2) | 16.0 ± 1.29 |
| PE:PC | (7:3) | 6.0 ± 1.87 |
| PE:PS | (7:3) | 13.0 ± 1.29 |
| PS:PC | (7:3) | 5.3 ± 1.58 |

*Fusion pH = 4.8, at a lipid concentration of 200 microM, n = 3.
+Calculated accordinq to eq. (1) expressed as mean ± standard deviation.

Although the PE:PHC (8:2) liposomes fused best, the fusion process was very leaky as indicated by experiments using calcein. At high concentrations calcein fluorescence is efficiently self-quenched, however, fluorescence is markedly enhanced when the dye is diluted as it leaks from the liposomes (Allen et al., *Biochim. Biophys. Acta, 597 418* (1980)). Table II shows that nearly all of the entrapped calcein in the PE:PHC (8:2) liposomes was rapidly released during fusion. However, if 40% cholesterol was included in these liposomes, less leakage of calcein was observed (55% latency). The cholesterol-containing liposomes were still efficiently fused as shown by the resonance energy transfer assay.

TABLE II

| Liposome Leakage During Fusion* | | | |
|---|---|---|---|
| | | Latency of calcein fluorescence # | |
| Liposome composition | % Fusion+ | Before fusion % | After fusion % |
| PE:PHC (8:2) | 89 ± 2.14 | 76 ± 2.88 | 5 ± .75 |
| PE:Chol:PHC (4:4:2) | 52 ± 2.37 | 71 ± 2.31 | 55 ± 1.21 |

*Fusion pH = 4.8, at a lipid concentration of 200 microM, n= 3.
+Calculated according to eq. (1) expressed as mean ± standard deviation.
Calculated according to eq. (2) expressed as mean ± standard deviation.

The liposomes formed by the method of the present invention will provide an effective cytoplasmic delivery system by fusing with the endosome membranes. The less leaky liposomes containing cholesterol will be particularly useful in discharging their contents into the cytoplasm. For example, foreign material such as drugs, enzymes, hormones, nutrients, antigens, antibodies (monoclonal or conventional), RNA, DNA (natural or recombinant) or any combinations of these and like substances, may be encapsulated in the pH sensitive liposomes of the present invention and ultimately be inserted into a living cell.

The term "living cell" as used above, means the cell of a living organism, plant or animal. For example, unicellular organisms such as yeasts, algae, fungi, bacteria and the like as well as multicellular organisms or systems including cell cultures (tumorous or benign) and whole animals such as mammals (including humans), reptiles, birds, and the like are contemplated herein.

Methods for encapsulating materials within liposomes are well known. For example, Szoka, Jr. et al., in U.S. Pat. No. 4,394,448 describe the incorporation of DNA into lipid vesicles and employing these liposomes to insert the DNA into living cells. Another useful encapsulation method employs a dialysis technique (Philippot et al., *Biochim. Biophys. Acta*, 716 140 (1982)). The methods taught by Szoka, Jr. et al. and Philippot et al. may be successfully employed for encapsulating DNA, RNA and other large molecular entities such as peptides and hormones, within the pH sensitive liposomes of the present invention. The Szoka, Jr. et al. and the Philippot et al. disclosures are incorporated herein by reference.

The first step in the preparation of encapsulated materials is to provide a mixture of a liposome forming composition in an organic solvent and an aqueous mixture of the material to be encapsulated. Alternatively, the material to be encapsulated, depending upon its solubility characteristics, may be dissolved in the organic solvent (e.g., chloroform). In either case, the liposomes may then be prepared by evaporation of the organic solvent, with the subsequent removal of the thin lipid film from the evaporation container using an aqueous buffer (e.g., phosphate buffered saline). Liposome forming compositions are generally well known, as are the methods for their preparation. See for example, Papahadjopoulos et al., U.S. Pat. No. 4,235,871, the disclosure of which is incorporated herein by reference.

As described herein, pH sensitive liposomes are prepared using phosphatidylethanolamine (PE) and palmitoyl homocysteine (PHC) in a molar ratio which may vary from one mole of PE for every nine moles of PHC to from nine moles of PE for every one mole of PHC. A preferred molar ratio has PE in excess by at least 3 moles to every 1 mole of PHC. The most preferred PE:PHC molar ratio is 4:1.

Materials and Methods

Materials: PHC was synthesized and purified using a well known method (Yatvin et al., *Science, supra*). Commercially available dioleoyl PE, dioleoyl PC and bovine brain PS were also used. All phospholipids including N-NBD-PE and N-RH-PE were purchased from Avanti (Birmingham, Ala.). Cholesterol and calcein were obtained from Sigma (St. Louis, Mo.).

Liposome Preparation: Solvent-free lipid films were suspended in PBS (pH 7.4) at 10 micromoles/ml and sonicated at room temperature for 15 min with a bath sonicator (Laboratory Supplies). Various lipid compositions were used as indicated. Fluorescence labelled liposomes containing 1 mol percent each of N-NBD-PE and N-RH-PE were prepared identically as the unlabelled liposomes.

Liposome Fusion: Ten microliters of labelled liposomes and various amounts of unlabelled liposomes were added to 2 ml PBS. After the relative fluorescence was measured, 5-20 microliters of aqueous 1 N HCl at various concentrations was added to achieve the desired pH while the sample was vigorously vortexed. After about 2 min at room temperature, an appropriate amount of aqueous 1 N NaOH was added to return the pH to 7.4. The relative fluorescence of the sample was again measured.

Fluorescence Measurements: A Perkin-Elmer LS 5 Fluorescence Spectrophotometer was used. The emission spectrum was taken for each sample which was excited at 468 nm. The excitation and emission slit widths were 5 nm and 3 nm respectively. Light scattering was about 5-6% of the total fluorescence signal. The ratio, R, of N-NBD-PE emission at 530 nm to the N-RH-PE emission at 580 nm is a sensitive measure of the efficiency of the resonance energy transfer between N-NBD-PE and N-RH-PE (Struck et al., supra). The value of R was 0.20 for the unfused liposomes, due to the high efficiency of energy transfer. As the labelled liposomes fused with the unlabelled liposomes, dilution of the fluorescent lipids occurred which resulted in a decrease in the efficiency of energy transfer and an increase in corresponding R values (Blumenthal et al., supra and Struck et al., supra). Hence the increase in R value is a quantitative measure for the degree of liposome fusion. A total mixing of lipids upon complete fusion would result in a maximal R value which is determined by the ratio of unlabelled to labelled liposomes in the fusion mixture. The percent of liposome fusion as defined herein was calculated as follows:

$$\% \text{ fusion} = \frac{R_f/R_{i-1}}{n} \times 100 \quad (1)$$

where $R_i$ and $R_f$ are the R values before and after the fusion reaction, respectively. The concentration ratio of unlabelled to labelled liposomes in the mixture is n. In order to check the validity of eq. (1), labelled and unlabelled liposomes were mixed at different ratios and the $R_i$ values were obtained. The plot of $R_f/R_{i-1}$ vs. n was a straight line with a slope equal to 45° up to n=3, indicating that eq. (1) was valid. For n>3 the fluorescence enhancement was lower than theoretical, therefore, most experiments were performed with n=3. The range of R values were reproducible to within ±5%.

Liposome Leakage: In order to determine liposome leakage during fusion, the water soluble self-quenching fluorescent dye, calcein, was used as an internal aqueous space marker (Allen et al., supra). Liposomes were prepared from lipid mixtures devoid of fluorescent phospholipids by sonication in PBS containing 140 mM calcein. The untrapped calcein was removed by passing liposomes through a Sepharose-4B column equilibrated in PBS. The calcein containing liposomes were treated with acid and base as described above. The calcein fluorescence before and after fusion, and after addition of 0.2% Triton X-100 to disrupt the liposomes, were measured at excitation and emission wavelengths of 490 and 518 nm, respectively. The latency of calcein fluorescence as defined herein was calculated as follows:

$$\% \text{ latency} = \left(1 - \frac{F}{F_t}\right) \times 100 \quad (2)$$

where F and $F_t$ are the calcein fluorescence intensity in the absence and presence of Triton X-100, respectively.

Electron Microscopy: Liposomes were negatively stained with 0.5% uranylacetate, and viewed in a Hitachi 600 electron microscope operating at 75 KV. Pictures were taken at 35,000×magnification and further enlarged photographically. To determine the size distribution of the liposomes a histogram was drawn by measuring >200 liposomes from micrographs taken of three different liposome preparations.

EXAMPLE 1

Fatty acid derivatized monoclonal antibody, anti-H2K$^k$, was incorporated into reverse-phase evaporation vesicles (REV) (Szoka Jr. et al., consisting of the fusion competent PE-PHC (8:2) liposomes of the present invention using a method similar to that of Shen et al., (*Biochim. Biophys. Acta*, 689 31 (1982). These immunoliposomes were then treated with PBS containing 140 mM calcein to serve as a marker.

Mouse L929 cells (K haplotype) were incubated with these marked immunoliposomes and upon fluorescent examination, diffuse fluorescence was noted throughout the cells, indicating that the calcein dye had been released into the cytoplasm.

In contrast, mouse cells incubated with PH insensitive immunoliposomes containing calcein, displayed only punctate fluorescence.

In a control experiment, mouse A31 cells (d haplotype) were incubated with the immunoliposomes of the present invention and no fluorescence was detectable.

EXAMPLE 2

Recombinant DNA, e.g., plasmid pBR322, containing a gene coding for the enzyme nitrogenase is encapsulated in the pH sensitive liposomes of the present invention using either the method of Example 1 or Philippot et al., supra. The liposomes are then added to potato protoplasts which actively endocytose the liposomes. The endocytosed liposomes fuse with the endosome membrane of the protoplasts and release the DNA into the cytoplasm of the cells. The DNA is integrated over time into the host genome and the nitrogenase activity is expressed. The protoplast is then regenerated into a whole potato plant which is capable of fixing nitrogen from the atmosphere, thereby increasing crop yield.

EXAMPLE 3

Recombinant DNA, e.g., plasmid pBR322, containing a growth hormone structural gene such as that of bovine growth hormone (see Miller et al., European Patent Appln. No. 47,600, based on 26.08.80 U.S. Pat. No. 181,348; or Fraser et al., European Patent Appln. No. 68,646 based on 08.06.81 U.S. Pat. No. 271,449) or the human pregrowth hormone (see Baxter et al., European Patent Appln. No. 20,147, based on 01.06.79 U.S. Pat. No. 44,647) is encapsulated, using either the method of Example 1 or the method of Philippot et al., supra, into the pH sensitive liposomes of the present invention containing, in addition to PE and PHC (8:2), lactosyl cerebroside (mol percent from 1 to 10). These liposomes are injected intravenously into an animal, such as calves, and selectively taken up by the hepatocytes of the liver. (Szoka, Jr., et al., Biochem. Biophys. Res. Comm., 110 140 (1983), incorporated herein by reference). The DNA is integrated into the genome over time and expressed generating excess amounts of growth hormone. The growth rate of the animal is thereby increased.

EXAMPLE 4

Recombinant DNA, e.g., plasmid pBR322, containing genes coding for viral antigens or fragments thereof, e.g., the hepatitis B genome (see Tiollais et al., U.K. Patent Appln. No. 2,034,323; or Galibert et al., U.S. Pat. No. 4,428,941) is encapsulated, using either the method of Example 1 or the method of Philippot et al., supra, into the pH sensitive liposomes of the present invention containing, in addition to PE and PHC (8:2), lactosyl cerebroside (mol percent from 1 to 10). These liposomes are injected intravenously-into young or adult animals (including mammals such as humans). Expression of the viral antigen or fragment thereof by the liver hepatocytes will elicit the body's immune response, producing antibodies against the antigen. The animal will thus be vaccinated against the viral infection.

What is claimed is:

1. A method of fusing liposomes which comprises:
   (a) preparing a suspension of liposomes containing at least one lipid which has a tendency to form the inverted hexagonal phase and at least 20 mol percent of one or more amphipathic molecules containing one or more weakly acidic functional groups selected from the group consisting of $C_{12}$ to $C_{30}$ fatty acids and palmitoyl homocysteine; and
   (b) in the absence of externally added divalent cations, proteins or other macromolecules, acidifying the liposome suspension to reduce the pH of these liposomes to below pH 7, whereby at least about 20% of said liposomes fuse to one another.

2. The method of claim 1 wherein said weakly acidic functional group of said amphipathic molecule is one or more carboxylic groups.

3. The method of claim 2, wherein said fusion occurs within the pH range of from about 4.8 to 6.8 and said amphipathic molecule is a $C_{16}$ to $C_{24}$ fatty acid.

4. The method of claim 3, wherein said long chain fatty acid is selected from the group consisting of palmitic acid and oleic acid.

5. The method of claim 2, from wherein said fusion occurs within the pH range of about 5.75 to 6.0 and said amphipathic molecule is palmitoylhomocysteine.

6. The method of claim 1 wherein the pH is reduced in step (b) to below 6.0.

7. The method of claim 1 wherein the pH is reduced in step (b) to below 5.0.

8. The method of claim 1 wherein step (b) is carried out using an aqueous mineral acid.

9. The method of claim 8, wherein the aqueous mineral acid is hydrochloric acid.

10. The method of claim 1 which further comprises forming the liposomes of step (a) with an amphipathic molecule which has a tendency to form hexagonal phase.

11. The method of claim 1, wherein said inverted hexagonal phase forming lipid of step (a) is selected from the group consisting of the phosphatidylethanolamines.

12. The method of claim 11, wherein the phosphatidylethanolamine is dioleoylophosphatidylethanolamine.

13. The method of claim 12 wherein the mol ratio of dioleoylphosphatidylethanolamine to said amphipathic molecule containing one or more weakly acidic functional groups is about 8:2.

14. The method of claim 13, wherein said amphipathic molecule containing one or more weakly acidic functional groups is selected from the group consisting of palmitoyl homocysteine, palmitic acid and oleic acid.

15. Fused nonagglomerated liposomes comprised of at least one lipid which has a tendency to form the inverted hexagonal phase and at least 20 mol percent of an amphipathic molecule containing one or more acidic functional groups an amphipathic molecule selected from palmitoylhomocysteine, palmitic acid and oleic acid.

16. The fused liposomes of claim 15, consisting of from 1:9 mol ratio of phosphatidylethanolamine and palmitoylhomocysteine.

17. The fused liposomes of claim 16 wherein the mol ratio of PE to PHC is from 5:1 to 1:5.

18. The fused liposomes of claim 16 wherein the mol ratio of PE to PHC is 8:2.

19. Fused liposomes containing phosphatidylethanolamine and oleic acid in a mol ratio of 8:2.

20. Fused liposomes containing phosphatidylethanolamine and palmitic acid in a mol ratio of 8:2.

* * * * *